US009078519B2

(12) United States Patent
Ulibarri

(10) Patent No.: US 9,078,519 B2
(45) Date of Patent: Jul. 14, 2015

(54) SAFETY GUARD FOR LIQUID STORAGE CABINET

(76) Inventor: Gilbert Ulibarri, Gentry, AR (US)

( * ) Notice: Subject to any disclaimer, the term of this patent is extended or adjusted under 35 U.S.C. 154(b) by 0 days.

(21) Appl. No.: 13/445,205

(22) Filed: Apr. 12, 2012

(65) Prior Publication Data

US 2013/0270985 A1 Oct. 17, 2013

(51) Int. Cl.

| | |
|---|---|
| ***A47B 97/00*** | (2006.01) |
| ***B01L 1/00*** | (2006.01) |
| ***A47B 88/00*** | (2006.01) |
| ***A61B 19/02*** | (2006.01) |
| ***A61C 19/02*** | (2006.01) |
| ***B01L 9/02*** | (2006.01) |
| ***A47B 81/00*** | (2006.01) |

(52) U.S. Cl.

CPC . *A47B 97/00* (2013.01); *B01L 1/50* (2013.01); *B01L 2200/082* (2013.01); *B01L 2300/041* (2013.01)

(58) Field of Classification Search

CPC ............ H02B 1/30; H02B 1/306; H02B 1/46; H02B 1/48; H02B 1/50; A47B 81/00; A47B 95/00; A47B 96/20; A47B 96/201; A47B 97/00; B01L 1/50; B01L 2200/082; B01L 2300/041

USPC .......................... 312/327, 328, 213, 290, 209

See application file for complete search history.

(56) References Cited

U.S. PATENT DOCUMENTS 1,002,642 A 9/1911 Carter
1,110,219 A 9/1914 Metzgar
1,362,421 A 12/1920 Imhoff
1,505,291 A * 8/1924 Schaefer, Jr. .................. 312/324
1,964,578 A 6/1934 Hunter
2,064,439 A * 12/1936 McWhirter ................... 312/296
2,484,933 A * 10/1949 Coyle et al. .................... 220/844
2,615,775 A * 10/1952 Claybourn et al. ........... 312/107
2,943,243 A 6/1960 Rachman et al.
3,101,226 A * 8/1963 Cochran, Jr. ............... 312/265.5
3,583,783 A * 6/1971 Murphy et al. ............... 206/736
3,633,783 A * 1/1972 Aue ......................... 220/592.06
3,942,669 A 3/1976 Savage, Jr.
3,995,674 A * 12/1976 Crawford ....................... 312/7.2
4,046,193 A * 9/1977 Dougherty ............... 165/104.21
4,128,285 A * 12/1978 Lore et al. ...................... 312/196
4,615,454 A 10/1986 Verhoog, Jr.
5,582,472 A 12/1996 Lyons et al.
5,779,537 A 7/1998 Alden
5,801,331 A * 9/1998 Zachrai ......................... 174/541
6,062,665 A * 5/2000 Schneider et al. ......... 312/265.6

(Continued)

OTHER PUBLICATIONS

Interstate Products, Inc., Weather Proof Safety Cabinets, www.interstateproducts.com/securall/cabinets/weather_proof_safety_cabinets.html (last visited Aug. 9, 2011).

(Continued)

*Primary Examiner* — Daniel J Troy
*Assistant Examiner* — Andrew Roersma
(74) *Attorney, Agent, or Firm* — Richard Blakely Glasgow

(57) ABSTRACT

A safety guard for a liquid storage cabinet having a substantially flat top surface, comprising a front panel; a pair of side panels, wherein said front panel is joined between said pair of side panels and forms an angle with the horizontal axis in the range of 20-60 degrees; a back panel, wherein said back panel is joined between said pair of side panels; and means for attaching said safety guard to said substantially flat top surface of said liquid storage container.

18 Claims, 3 Drawing Sheets

(56) References Cited

U.S. PATENT DOCUMENTS

| | | | | |
|---|---|---|---|---|
| 6,088,225 | A | 7/2000 | Parry et al. | |
| 6,153,857 | A * | 11/2000 | Gunnels | 219/386 |
| 6,378,962 | B1 * | 4/2002 | Green | 312/137 |
| 6,478,391 | B1 * | 11/2002 | Stoever | 312/265.5 |
| 6,877,827 | B2 * | 4/2005 | Holighaus et al. | 312/223.1 |
| 6,932,443 | B1 * | 8/2005 | Kaplan et al. | 312/213 |
| 6,953,149 | B2 | 10/2005 | Taylor | |
| 2007/0205703 | A1 | 9/2007 | McLuckie et al. | |
| 2008/0211363 | A1 | 9/2008 | Carter et al. | |
| 2009/0085447 | A1 | 4/2009 | McLuckie et al. | |
| 2009/0091220 | A1 | 4/2009 | Eyer et al. | |
| 2009/0255089 | A1 * | 10/2009 | Boonmatun | 16/231 |

OTHER PUBLICATIONS

Global Industrial, Weatherproof Flammable Safety Cabinets, www.globalindustrial.com/g/storage/flammable-osha-cabinets/flammable/weatherproof.htm (last visited Aug. 9, 2011).

CableOrganizer.Com, Greenlee 2260 Slant Top Box, http://cableorganizer.com/greenless/tool-boxes/slant-top-tool-boxes.htm (last visited Aug. 9, 2011).

ESE Direct, Flammable Storage Sloping Top Bin, www.esedirect.co.uk/p-438-flammable-storage-sloping-top-bin.aspx (last visited Aug. 9, 2011).

* cited by examiner

SAFETY GUARD FOR LIQUID STORAGE CABINET

CROSS-REFERENCE TO RELATED APPLICATIONS

Not applicable

STATEMENT REGARDING FEDERALLY SPONSORED RESEARCH OR DEVELOPMENT

Not applicable

BACKGROUND OF THE INVENTION

1. Field of the Invention

The present invention relates generally to a liquid storage cabinet and, more particularly, to a safety guard for attachment to a liquid storage cabinet.

2. Brief Description of the Related Art

Containers of chemicals, paints, and other flammable compounds must be carefully stored. Such storage is required to meet specific requirements and specifications, such as those set forth by the Occupational Safety & Health Administration (OSHA). For example, flammable liquid storage cabinets must comply with OSHA regulations as to the venting of the cabinet, size of the cabinet, materials used to manufacture the cabinet, and the fire resistance qualities of the cabinet, among other requirements. Liquid storage cabinets which comply with OSHA regulations are well-known in the prior art.

Many of the prior art liquid storage cabinets are rectangular-shaped cabinets having doors on the front of the cabinet to access the internal storage compartment. Because these prior art cabinets have a flat top surface, from the inventor's experience, it is common for flammable liquid containers to be placed on top of the cabinet, instead of being properly stored inside the cabinet. The presence of flammable liquid containers on top of the storage cabinet poses a significant risk of the flammable liquids being spilled. This risk of spillage creates the potential for burns or other bodily harm if the liquids come in contact with people in the area.

It would therefore be desirable to develop a safety guard for flat top flammable liquid storage cabinets that is effective to prevent the placement of objects, including flammable liquid containers, on its surface.

BRIEF SUMMARY OF THE INVENTION

The present invention is directed to a safety guard for a liquid storage cabinet having a substantially flat top surface, comprising: (a) a front panel; (b) a pair of side panels, wherein said front panel is joined between said pair of side panels and forms an angle with the horizontal axis in the range of 20-60 degrees; (c) a back panel, wherein said back panel is joined between said pair of side panels; and (d) means for attaching said safety guard to said substantially flat top surface of said liquid storage cabinet.

These and other features, objects and advantages of the present invention will become better understood from a consideration of the following detailed description of the preferred embodiments and appended claims in conjunction with the drawings as described following:

DETAILED DESCRIPTION OF THE INVENTION

Figure 1:
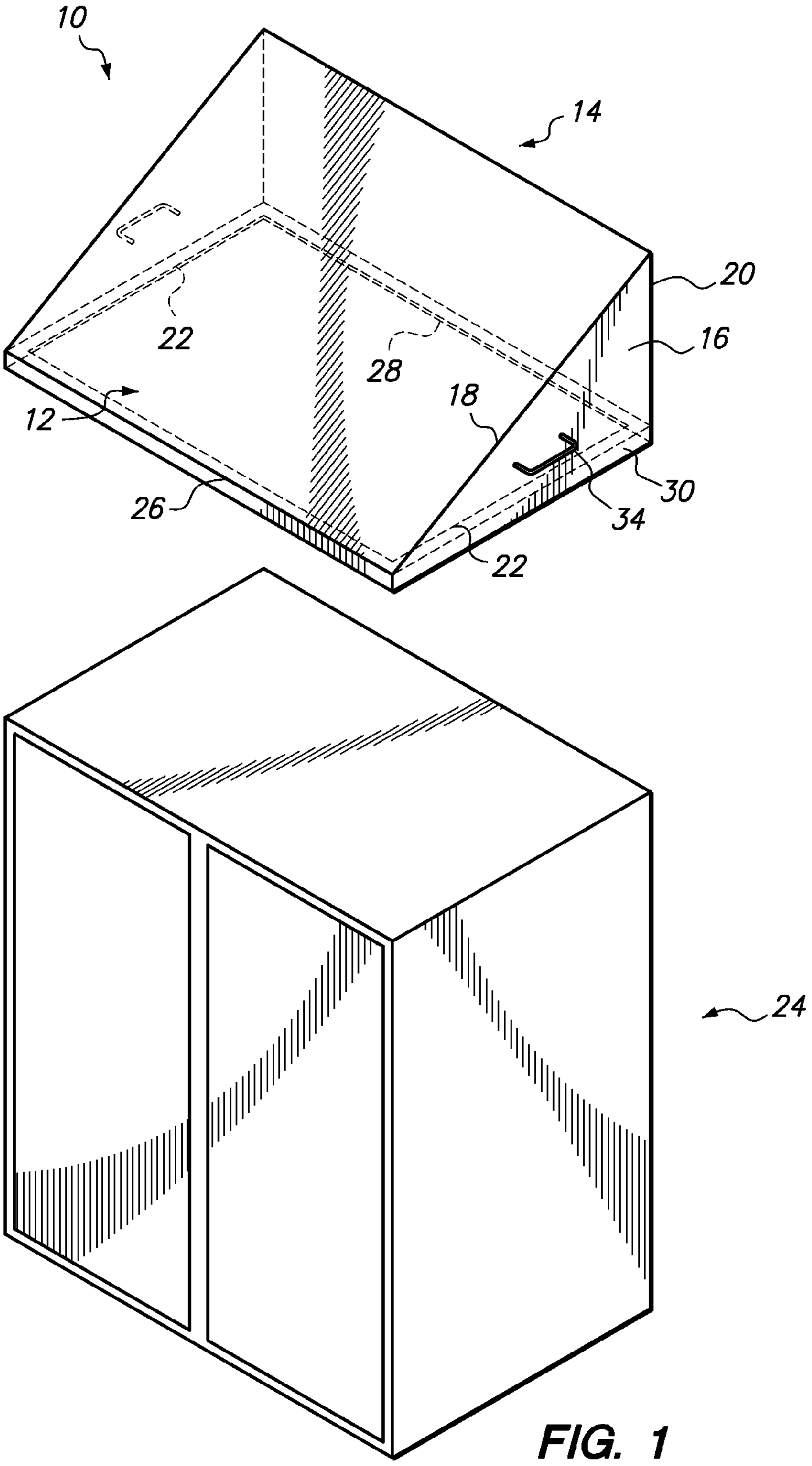
FIG. 1 is an exploded perspective view of the first preferred embodiment of the present invention.

With reference to FIGS. 1-5, the safety guard 10 comprises a front panel 12, a back panel 14, and a pair of side panels 16. The panels are joined to one another to form the safety guard 10. The safety guard 10 preferably is wedged-shaped, and has an open bottom and a hollow interior. The front panel 12, back panel 14, and side panels 16 are preferably made of 18-gauge galvanized steel or plastic, however, the panels may be made of any material that is durable and substantially rigid (e.g. PLEXIGLASS®). The front panel 12 is a substantially flat plate, preferably square or rectangular in shape. The side panels 16 are triangular-shaped, preferably in the shape of a right triangle. The front panel 12 is joined to the side panels 16 at its left and right sides. Each side panel 16 is joined to the front panel 12 along its longest side 18. The back panel 14 is a substantially flat plate and is preferably square or rectangular. The back panel 14 is joined to the side panels 16 at its left and right sides, and is joined to the front panel 12 at its top side. Each side panel 16 is joined to the back panel 14 along its shortest side 20. The third side 22 of each side panel 16 abuts the top surface of a liquid storage cabinet 24 when the safety guard 10 is attached to the cabinet 24.

When joined to the side panels 16, the front panel 12 is elevated from its front end to its back end at an angle α in the range of 20-60 degrees (23.5-30 degrees is preferable) with respect to the horizontal axis. The front end of the front panel 12 corresponds to the front surface of the cabinet 24, while the back end of the front panel 12 corresponds to the back surface of the cabinet 24. Thus, when the safety guard 10 is attached to the cabinet 24, the front panel 12 of the safety guard 10 slopes from the back of the cabinet 24 to the front of the cabinet 24.

In one embodiment, the front panel 12, back panel 14, and side panels 16 are joined by means well-known to those skilled in the art, including, but not limited to, rivets. In another embodiment, the front panel 12, back panel 14, and side panels 16 are produced as a single piece (e.g. molded or welded) of steel or plastic.

The front panel 12 may be hinged to the back panel 14 to allow access under the safety guard 10, thus permitting storage of non-flammable materials or other items (e.g. rags and mop heads) on top of the cabinet 24.

Figure 2:
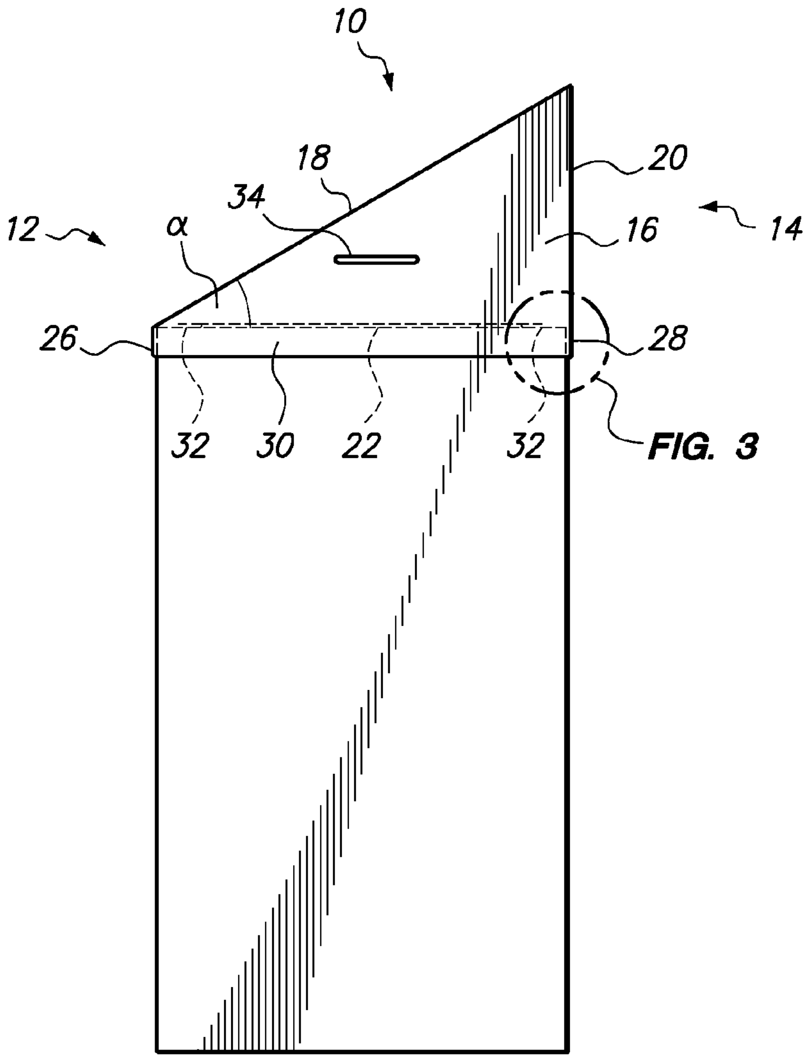
FIG. 2 is a side view of the first preferred embodiment of the present invention.
Figure 3:
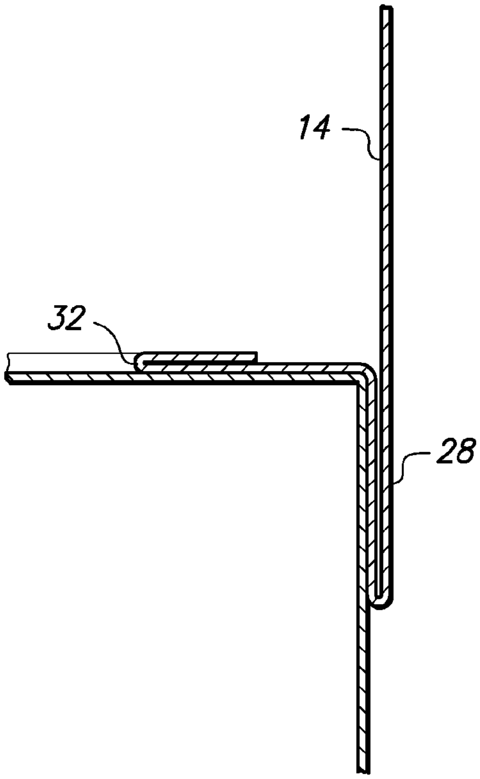
FIG. 3 is a detailed cut-away view of FIG. 2.

In a first embodiment, as shown in FIGS. 1-3, the safety guard 10 is releasably attached to the liquid storage cabinet 24. A front panel lip 26 is joined to the front panel 12 and extends downwardly from the bottom of the front end of the front panel 12. The lip 26 contacts the front surface of the cabinet 24 when the safety guard 10 is placed on the top of the cabinet 24. The front panel 12 and the lip 26 may either be joined by means well-known to those skilled in the art (e.g. rivets) or produced as a single piece (e.g. molded or welded) of steel or plastic. The lip 26 preferably extends the entire width of the front panel 12. While the height of the lip 26 may vary, the lip 26 does not interfere with the opening and closing of the doors on the front of the cabinet 24. The contact between the lip 26 and the cabinet 24 results in a tight fit of the safety guard 10 to the front surface of the cabinet 24.

The back panel 14 is joined to a back panel lip 28 that extends downwardly from the bottom of the back panel 14.

The lip 28 contacts the back surface of the cabinet 24 when the safety guard 10 is placed on the top of the cabinet 24. The back panel 14 and the lip 28 may either be joined by means well-known to those skilled in the art (e.g. rivets) or produced as a single piece (e.g. molded or welded) of steel or plastic. The lip 28 preferably extends the entire width of the back panel 12. The contact between the lip 28 and the cabinet 24 results in a tight fit of the safety guard 10 to the back surface of the cabinet 24.

Each of the two side panels 16 are joined to a side panel lip 30 that extends downwardly from the third side 22 of each side panel 16. The lip 30 contacts the side surface of the cabinet 24 when the safety guard 10 is placed on the top of the cabinet 24. The side panel lip 30 and the side panel 16 may either be joined by means well-known to those skilled in art (e.g. rivets) or produced as a single piece (e.g. molded or welded) of steel or plastic. The lip 30 preferably extends the entire width of the side panel 16. The contact between the lip 30 and the cabinet 24 results in a tight fit of the safety guard 10 to the side surface of the cabinet 24.

To provide further support, the front panel 12, side panels 16, and back panel 14 may each be joined to a support plate 32. The support plate 32 is joined to the front panel 12 at its front end and is joined to the side panels 16 at their third sides. The support plate 32 is joined to the back panel 14 at its bottom end. The support plate 32 is preferably joined to the side panels 16 and the back panel 14 at a 90 degree angle, while it is joined to the front panel at an angle in the range of 20-60 degrees (23.5-30 degrees is preferable). Each support plate 32 extends horizontally under the covering provided by the guard 10 when it is attached to the cabinet. The support plate 32 preferably extends the entire length of each panel and is one inch in width. When the safety guard 10 is attached to the cabinet 24, each plate 32 contacts and rests on the top surface of the cabinet 24. The support plate 32 aids in providing a sturdy connection between the safety guard 10 and the cabinet 24. In combination, the lips 26, 28, 30 and the support plates 32 provide stability when the guard 10 is attached to the cabinet 24, including preventing the guard 10 from sliding off of the top surface of the cabinet 24.

Each panel 12, 14, 16 of the safety guard 10 may be joined to its associated lip (26 or 28 or 30) and support plate 32 by means well-known to those skilled in the art (e.g. rivets) or produced as a single piece (e.g. molded or welded) of steel or plastic. For example, the steel sheet that preferably comprises the back panel 14 is capable of forming a hairpin loop at one end by folding back on itself. As shown in FIG. 3, the folding over forms both the lip 28 and the support plate 32. The double-layer of steel creates additional stability for the lip 30 and the support plate 32. The lips 26, 30 and the support plates 32 associated with the front panel 12 and side panels 16 may also be formed similarly from a single piece of metal.

In the first embodiment, the safety guard 10 can only be removed by pulling the safety guard 10 vertically from the top of the cabinet 24, thus disengaging the safety guard from the cabinet. This causes an interference with the contact points between front panel lip 26 and cabinet 24, the back panel lip 28 and cabinet 24, and the side panel lips 30 and cabinet 24. The safety guard 10 may also have two handles 34 of the kind well-known to those skilled in the art. The handles 34 may be grasped to remove the guard from the cabinet 24.

Figure 4:
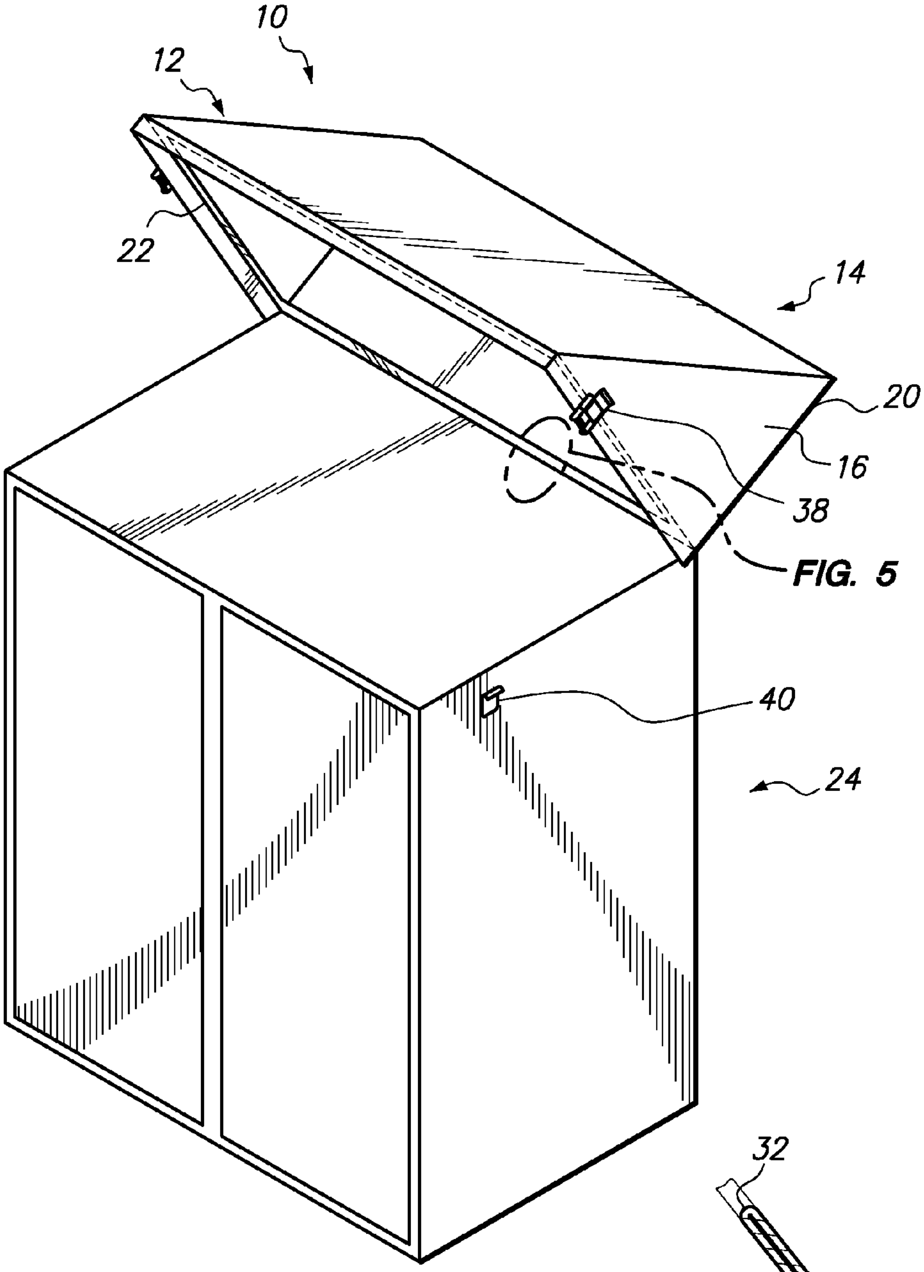
FIG. 4 is a perspective view of the second preferred embodiment of the present invention.
Figure 5:
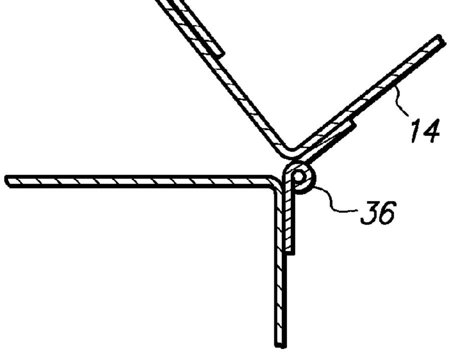
FIG. 5 is a detailed cut-away view of FIG. 4.

In a second embodiment, as shown in FIGS. 4-5, the safety guard 10 is permanently attached to the cabinet 24. In this embodiment, a hinge 36 connects the back panel 14 and the back surface of the cabinet 24. In this embodiment, the safety guard 10 has an open and closed position. When the safety guard 10 is resting on the top surface of the cabinet 24, the safety guard 10 is in the closed position. Alternatively, when the safety guard 10 is lifted from the surface of the cabinet 24 and pivots via the hinge, the safety guard 10 is in the open position. When the safety guard 10 is in the open position, a person may easily place or remove non-flammable liquids or other items (e.g. rags and mop heads) on the top of the cabinet 24 for safe storage. The safety guard 10 may have a buckle 38 attached to each of the side panels 16. The buckle is preferably attached to the side panel two inches from the front end of the front panel 12. A keeper 40 is attached to the two side surfaces of the cabinet 24 to engage the buckle 38 and secure the safety guard 10 to the cabinet 24. The buckle 38 and keeper 40 are preferably of the kind well-known to those skilled in the art.

The attachment of the safety guard 10 to the top surface of the cabinet 24 prevents objects, including flammable liquid storage containers, from being placed directly on the top surface of the cabinet 24. The slope of the safety guard 10 also prevents objects from being placed on the front panel 12 of the safety guard 10.

The present invention has been described with reference to certain preferred and alternative embodiments that are intended to be exemplary only and not limiting to the full scope of the present invention as set forth in the appended claims.

I claim:

1. A safety guard for a liquid storage cabinet having an open and a closed position, comprising:

(a) a front panel comprising a first end and a second end;

(b) a first side panel and a second side panel, wherein said front panel is joined between said first side panel and said second side panel, and wherein said front panel forms an angle with the horizontal axis;

(c) a back panel, wherein said back panel is joined between said first side panel and said second side panel;

(d) a first side support plate and a second side support plate, wherein said first side support plate and said second side support plate rest on a substantially flat top surface of a liquid storage cabinet when said safety guard is in said closed position, thereby forming an internal compartment between said safety guard and said substantially flat top surface of said liquid storage cabinet for storing nonflammable liquids, wherein an area of said substantially flat top surface of said liquid storage cabinet is exposed between said first side support plate and said second side support plate when said safety guard is in said closed position, wherein said first side support plate and said second side support plate are raised from said substantially flat top surface of said liquid storage cabinet when said safety guard is in said open position; and (e) a first side lip and a second side lip, wherein said first side panel, said first side support plate, and said first side lip are formed in a single and continuous sheet of a building material, wherein said first side panel segues into said first side lip and said first side lip segues into said first side support plate, wherein said second side panel, said second side support plate, and said second side lip are formed in a single and continuous sheet of said building material, wherein said second side panel segues into said second side lip and said second side lip segues into said second side support plate, wherein said first side lip and said second side lip extend below the substantially flat top surface of the liquid storage cabinet.

2. The safety guard of claim 1 further comprising a front lip, wherein said front lip is joined to said first end of said front panel.

3. The safety guard of claim 1 further comprising a back lip, wherein said back lip is joined to said back panel.

4. The safety guard of claim 1 further comprising a front support plate, wherein said front support plate is joined to said front panel.

5. The safety guard of claim 1 further comprising a back support plate, wherein said back support plate is joined to said back panel.

6. The safety guard of claim 1 further comprising a hinge, wherein said hinge connects said back panel to a liquid storage cabinet.

7. The safety guard of claim 1 wherein said angle is in the range of 20-60 degrees.

8. The safety guard of claim 1 wherein said back panel is joined to said second end of said front panel.

9. The safety guard of claim 1 further comprising two handles, wherein said handles are connected to said pair of side panels.

10. The safety guard of claim 1, wherein said first side support plate extends perpendicularly from said first side panel when said safety guard is in said open position and said closed position, and said second side support plate extends perpendicularly from said second side panel when said safety guard is in said open position and said closed position.

11. The safety guard of claim 1, wherein said building material comprises steel or plastic.

12. A safety guard for a liquid storage cabinet having an open and closed position, comprising:

(a) a front panel comprising a first end and a second end;

(b) a first side panel and a second side panel, wherein said front panel is joined between said first side panel and said second side panel, and wherein said front panel forms an angle with the horizontal axis;

(c) a back panel, wherein said back panel is joined between said first side panel and said second side panel;

(d) a hinge, wherein said hinge connects said back panel to a liquid storage cabinet;

(e) a first side support plate and a second side support plate, wherein said first side support plate and said second side support plate rest on a substantially flat top surface of a liquid storage cabinet when said safety guard is in said closed position, thereby forming an internal compartment between said safety guard and said substantially flat top surface of said liquid storage cabinet for storing nonflammable liquids, wherein an area of said substantially flat top surface of said liquid storage cabinet is exposed between said first side support plate and said second side support plate when said safety guard is in said closed position, wherein said first side support plate and said second side support plate are raised from said substantially flat top surface of said liquid storage cabinet when said safety guard is in said open position; and (f) a first side lip and a second side lip, wherein said first side panel, said first side support plate, and said first side lip are formed in a single and continuous sheet of a building material, wherein said first side panel segues into said first side lip and said first side lip segues into said first side support plate, wherein said second side panel, said second side support plate, and said second side lip are formed in a single and continuous sheet of said building material, wherein said second side panel segues into said second side lip and said second side lip segues into said second side support plate, wherein said first side lip and said second side lip extend below the substantially flat top surface of the liquid storage cabinet.

13. The safety guard of claim 12 further comprising a front lip, wherein said front lip is joined to said first end of said front panel.

14. The safety guard of claim 12 further comprising a back lip, wherein said back lip is joined to said back panel.

15. The safety guard of claim 12 further comprising a front support plate, wherein said front support plate is joined to said front panel.

16. The safety guard of claim 12 further comprising a back support plate, wherein said back support plate is joined to said back panel.

17. The safety guard of claim 12, wherein said first side support plate extends perpendicularly from said first side panel when said safety guard is in said open position and said closed position, and said second side support plate extends perpendicularly from said second side panel when said safety guard is in said open position and said closed position.

18. The safety guard of claim 12, wherein said building material comprises steel or plastic.

* * * * *